(12) United States Patent
Swerdlow

(10) Patent No.: US 8,825,158 B2
(45) Date of Patent: Sep. 2, 2014

(54) METHOD AND APPARATUS FOR DETECTION OF LEAD CONDUCTOR ANOMALIES USING DYNAMIC ELECTRICAL PARAMETERS

(75) Inventor: Charles Swerdlow, Los Angeles, CA (US)

(73) Assignee: Lamda Nu, LLC, Orono, MN (US)

( * ) Notice: Subject to any disclaimer, the term of this patent is extended or adjusted under 35 U.S.C. 154(b) by 0 days.

(21) Appl. No.: 12/868,056

(22) Filed: Aug. 25, 2010

(65) Prior Publication Data

US 2011/0054554 A1    Mar. 3, 2011

Related U.S. Application Data

(60) Provisional application No. 61/236,586, filed on Aug. 25, 2009.

(51) Int. Cl.
*A61N 1/08* (2006.01)

(52) U.S. Cl.
USPC ............................ 607/27; 607/28; 607/29

(58) Field of Classification Search
USPC ...................................... 607/27–29
See application file for complete search history.

(56) References Cited

U.S. PATENT DOCUMENTS

| | | | |
|---|---|---|---|
| 3,599,055 A | 8/1971 | Bloom | |
| 4,766,549 A | 8/1988 | Schweitzer, III et al. | |
| 5,003,975 A | 4/1991 | Hafelfinger et al. | |
| 5,231,987 A * | 8/1993 | Robson | 607/29 |
| 5,243,980 A | 9/1993 | Mehra | |
| 5,405,363 A | 4/1995 | Kroll et al. | |
| 5,741,311 A | 4/1998 | McVenes et al. | |
| 5,755,742 A | 5/1998 | Schuelke et al. | |
| 5,897,577 A | 4/1999 | Cinbis et al. | |
| 5,944,746 A | 8/1999 | Kroll | |
| 6,104,954 A | 8/2000 | Blunsden | |
| 6,928,325 B2 | 8/2005 | Zhu et al. | |
| 7,047,083 B2 | 5/2006 | Gunderson et al. | |
| 7,081,130 B2 | 7/2006 | Jang | |
| 7,120,563 B2 | 10/2006 | Bechhoefer et al. | |
| 7,289,851 B2 | 10/2007 | Gunderson et al. | |

(Continued)

FOREIGN PATENT DOCUMENTS

| EP | 0288630 B1 | 11/1988 |
|---|---|---|
| EP | 2032027 B1 | 10/2011 |

OTHER PUBLICATIONS

Lo et al., Noise-Domain Reflectometry for Locating Wiring Faults, IEEE Transactions on Electromagnetic Compatibility, vol. 47, No. 1, Feb. 2005, 8 pages.

(Continued)

*Primary Examiner* — Joseph Stoklosa
(74) *Attorney, Agent, or Firm* — Patterson Thuente Pedersen, P.A.

(57) ABSTRACT

A method and apparatus to detect anomalies in the conductors of leads attached to implantable medical devices based on the dynamical electrical changes these anomalies cause. In one embodiment, impedance is measured for weak input signals of different applied frequencies, and a conductor anomaly is detected based on differences in impedance measured at different frequencies. In another embodiment, a transient input signal is applied to the conductor, and an anomaly is identified based on parameters related to the time course of the voltage or current response, which is altered by anomaly-related changes in capacitance and inductance, even if resistance is unchanged. The method may be implemented in the implantable medical device or in a programmer used for testing leads.

19 Claims, 7 Drawing Sheets

(56) References Cited

U.S. PATENT DOCUMENTS

| | | | |
|---|---|---|---|
| 7,369,893 | B2 | 5/2008 | Gunderson |
| 7,454,249 | B1 | 11/2008 | Bornzin et al. |
| 7,747,320 | B1 | 6/2010 | Kroll et al. |
| 7,764,998 | B1 | 7/2010 | Raddatz |
| 8,200,330 | B2 | 6/2012 | Kroll et al. |
| 8,352,033 | B2 | 1/2013 | Kroll |
| 8,467,872 | B2 | 6/2013 | Hareland |
| 8,577,457 | B2 | 11/2013 | Miller et al. |
| 8,700,156 | B2 | 4/2014 | Kroll |
| 2004/0010303 | A1 | 1/2004 | Bolea et al. |
| 2004/0068301 | A1 | 4/2004 | Waltman et al. |
| 2004/0158290 | A1 | 8/2004 | Girouard et al. |
| 2005/0187586 | A1 | 8/2005 | David et al. |
| 2005/0256547 | A1* | 11/2005 | Stahmann et al. ............ 607/27 |
| 2006/0135886 | A1 | 6/2006 | Lippert et al. |
| 2006/0241513 | A1 | 10/2006 | Hatlestad |
| 2006/0265038 | A1 | 11/2006 | Hagen et al. |
| 2007/0208387 | A1 | 9/2007 | Mower |
| 2008/0208271 | A1 | 8/2008 | Sih et al. |
| 2008/0309351 | A1 | 12/2008 | Stewart et al. |
| 2009/0099615 | A1 | 4/2009 | Kroll |
| 2009/0292331 | A1 | 11/2009 | Gunderson et al. |
| 2010/0228307 | A1 | 9/2010 | Kroll et al. |
| 2011/0054554 | A1 | 3/2011 | Swerdlow |
| 2011/0054558 | A1 | 3/2011 | Gunderson et al. |
| 2011/0160829 | A1 | 6/2011 | Foster et al. |
| 2012/0035491 | A1 | 2/2012 | Mahajan et al. |
| 2013/0123871 | A1 | 5/2013 | Kroll |
| 2013/0325079 | A1 | 12/2013 | Kroll et al. |
| 2013/0325080 | A1 | 12/2013 | Kroll et al. |

OTHER PUBLICATIONS

"Agilent Impedance Measurement Handbook a Guide to Measurement Technology and Techniques 4th Edition," Agilent Technologies, Inc., Jun. 17, 2009, 140 pages.

Armour, Andrew J., et al., "Gross and Microscopic Anatomy of the Human Intrinsic Cardiac Nervous System," Anatomical Record, 1997, pp. 289-298.

Balkhy, Husam H., et al., "Autonomic Ganglionated Plexi: Characterization and Effect of Epicardial Microwave Ablation in a Canine Model of Vagally Induced Actue Atrial Fibrillation," Meeting for the International Society for Minimally Invasive Cardiothoracic Surgery (Abstract), 2006.

Brewer et al., "Low Voltage Shocks Have a Significantly Higher Tilt of the Internal Electric Field Than Do High Voltage Shocks," Angeion Corporation, Jan. 1995, Part II, PACE, vol. 18, pp. 214-220.

Chevalier, P., "Quantitative Study of Nerves of the Human Left Atrium," Heart Rhythm, 2005, pp. 518-522.

Dilling-Boer, Dagmara et al., "Ablation of Focally Induced Atrial Fibrillation: Selective or Extensive?," J. Cardio. Electryphys., 2004, pp. 200-205.

Haissaguerre, Michel et al., "Pulmonary Veins in the Substrate for Atrial Fibrillation: The "venous wave" Hypothesis," 2004, pp. 2290-2292.

Haissaguerre, Michel et al., "Spontaneous Initiation of Atrial Fibrillation by Ecoptic Beats Originating in the Pulmonary Veins," NEJM, 2006, pp. 659-666.

Kilgore, K.L., et al., "Nerve Conduction Block Utilising High-Frequency Alternating Current," Med. Biol. Eng. Comput., 2004, pp. 394-406.

Kumagai, K., et al., "Electrophysiologic Properties of Pulmonary Veins Assessed Using a Multielectrode Basket Catheter," 2004, pp. 2281-2289.

Levy, S., "Characterization of Different Subsets of Atrial Fibrillation in General Practice in France: The ALFA Study," The College of French Cardiologists, Circulation, 1999, pp. 3028-3035.

Nathan, H., et al., "The Junction Between the Left Atrium and the Pulmonary Veins: An Anatomic Study of Human Hearts," Circulation, 1966, pp. 412-422.

Oh., S., "Vagal Denervation and Atrial Fibrillation Inducibility: Epicardial Fat Pad Ablation Does Not Have Long-Term Effects," Heart Rhythm, 2006, pp. 701-708.

Oral, Hakan et al., "Pulmonary Vein Isolation for Paroxysmal and Persistent Atrial Fibrillation," Circulation, 2002, pp. 1077-1081.

Pappone, Carlo, "Pulmonary Vein Denervation Enhances Long-Term Benefit After Circumferential Ablation for Paroxysmal Atrial Fibrillation," Circulation, 2004, pp. 327-334.

Patterson, E. et al., "Triggered Firing in Pulmonary Veins Initiated by In Vitro autonomic nerve stimulation," Heart Rhythm, 2005, pp. 624-631.

Patterson, Eugene et al., "Sodium-Calcium Exchange Initiated by the Ca2+ Transient: An Arrhythimia Trigger Within Pulmonary Veins," J. Am. Coll. Cardiol, 2006, pp. 1196-1206.

Po Sunny S., et al., "Rapid and Stable Re-entry within the Pulmonary Vein as a Mechanism Initiating Paroxysmal Atrial Fibrillation," J.Am Coll. Cariol., 2005, pp. 1871-1877.

Po, Sunny S. et al., "Experimental Model for Paroxysmal Atrial Fibrillation Arising at the Pulmonary Vein-Atrial Junctions," Heart Rhythm, 2006, pp. 201-208.

Randall, David C., et al., "Ablation of Posterior Atrial Ganglionated Plexus Potentiates Sympathetic Tachycardia to Behavioral Stress," Comp. Physiol., 1998, pp. 779-787.

Schauerte, P., et al., "Ventricular Rate Control During Atrial Fibrillation by Cardiac Parasympathetic Nerve Stimulation: A Transvenous Approach," J. Am. Coll. Cardiol., 1999, pp. 2043-2050.

Schauerte, Patrick et al., "Catheter Ablation of Cardiac Autonomic Nerves for Prevention of Vagal Atrial Fibrillation," Circulation, 2000, pp. 2774-2780.

Schauerte, Patrick, "Focal Atrial Fibrillation: Experimental Evidence for a Pathophysiologic Role of the Autonomic Nervous System," Cardiovasc Electrophysiol., 2001, pp. 592-599.

Scherlag, Benjamin J., et al., "Autonomically Induced Conversion of Pulmonary Vein Focal Firing Into Atrial Fibrillation," J. Am Coll. Cardiol., 2005, pp. 1878-1886.

Scherlag, Benjamin, "Electrical Stimulation to Identify Neural Elements on the Heart: Their Role in Atrial Fibrillation," J. Interv. Card, Electrophysiol, 2005, pp. 37-42.

Tai, C., "Stimulation Analysis of Conduction Block in Unmyelinated Axons Induced by High-Frequency Biphasic Electrical Currents," IEEE T-BME, 2005, p. 1323.

Tchou et al., "The AngeMed Sentinel Implantable Antitachycardia Pacer Cardioverter-Defibrillator," Implantable Cardioverter-Defibrillators: A Comprehensive Textbook, Copyright 1994, pp. 755-761.

Tomasic, "Acute and Chronic High-Frequency Properties of Cardiac Pacing and Defibrillation Leads," Med Biol Eng Comput 50:827-837, 2012.

Ellenbogen, "Performance of ICD Lead Integrity Alert to Assist in the Clinical Diagnosis of ICD Lead Failures: Analysis of Different ICD Leads," Circulation Arrhythmia and Electrophysiology, Oct. 7, 2013.

Swerdlow, "Downloadable Algorithm to Reduce Inappropriate Shocks Caused by Fractures of Implantable Cardioverter-Defibrillator Leads," Circulation Journal of the American Heart Association, Nov. 3, 2008, 9 pages.

Swerdlow, "Downloadable Software Algorithm Reduces Inappropriate Shocks Caused by Implantable Cardioverter-Defibrillator Lead Fractures—A Prospective Study," Circulation Journal of the American Heart Association, Sep. 27, 2010, 8 pages.

PCT Application No. PCT/US2013/043386, filed May 30, 2013, Search Report and Written Opinion dated Sep. 27, 2013, 10 pages.

PCT Application No. PCT/US2013/043389, filed May 30, 2013, Search Report and Written Opinion dated Sep. 5, 2013, 9 pages.

Application and File history for U.S. Appl. No. 13/735,599, filed Jan. 7, 2013. Inventor Kroll.

Application and File history for U.S. Appl. No. 13/842,838, filed Mar. 15, 2013. Inventor Kroll.

Application and File history for U.S. Appl. No. 12/252,310, filed Oct. 15, 2008. Inventor: Kroll.

Application and File history for U.S. Appl. No. 13/843,145, filed Mar. 15, 2013. Inventors: Kroll et al.

Application and File history for U.S. Appl. No. 13/833,477, filed Mar. 15, 2013. Inventors: Kroll et al.

* cited by examiner

METHOD AND APPARATUS FOR DETECTION OF LEAD CONDUCTOR ANOMALIES USING DYNAMIC ELECTRICAL PARAMETERS

CROSS-REFERENCE TO RELATED APPLICATIONS

This application claims the benefit under 35 U.S.C. §119 (e) of U.S. Provisional Patent Application Ser. No. 61/236,586, filed Aug. 25, 2009, which is hereby incorporated by reference.

BACKGROUND OF THE INVENTION

1. Field of the Invention

The present invention relates, generally, to scientific and medical systems, apparatus and methods. More particularly, the invention relates to method and apparatus for diagnosis of conductor anomalies. Most particularly, the invention relates to a method and apparatus for diagnosis of conductor anomalies in an implantable medical device, such as an implantable cardioverter defibrillator (ICD), a pacemaker, or a neurostimulator.

2. Background Information

Anomalies of conductors in implantable medical devices constitute a major cause of morbidity. Examples of such devices include pacemakers, implantable cardioverter defibrillators (ICDs), and neurostimulators. For example, early diagnosis of ICD lead conductor anomalies is important to reduce morbidity and/or mortality from loss of pacing, inappropriate ICD shocks, and/or ineffective treatment of ventricular tachycardia or fibrillation (ventricular fibrillation).

Multilumen ICD defibrillation electrodes include both one or more high-voltage conductors and one or more pace-sense conductors. Pace-sense lead fractures commonly present as inappropriate shocks caused by oversensing of lead-related nonphysiological potentials, commonly referred to as lead "noise" signals, caused by the conductor anomalies. Functional failure of an ICD's pace-sense conductor may result in symptoms caused by loss of pacing functions for bradycardia rate support, cardiac resynchronization, or antitachycardia pacing.

Thus one major goal is high sensitivity of diagnosis: identification of lead conductor anomalies at the subclinical stage, before they present as a clinical problem. A second major goal is high specificity: A false positive provisional clinical diagnosis of lead conductor anomaly produces patient anxiety and results in potentially-avoidable diagnostic testing. A false positive confirmed clinical diagnosis results in unnecessary lead replacement, with corresponding expense and risk.

Existing technology for diagnosis of conductor anomalies in an implantable medical device is believed to have significant limitations and shortcomings.

The primary method in the prior art for monitoring pacemaker and ICD lead integrity is periodic measurement of electrical resistance, commonly referred to as "impedance monitoring." Impedance monitoring uses single pulses. Various methods are well-known in the art. These methods provide a value of impedance close to the direct-current resistance.

In the circuit being measured, most of the resistance is at the electrode-tissue interface of the high-resistance tip electrode, and variations of up to 10% in this value are common. Each individual pace-sense conductor (for example, the conductor to the tip electrode or the ring electrode) contributes less than 10% to the measured resistance. In some ICD leads, this value is as less than as 3%. Thus even if the resistance in a single conductor doubled or tripled, the overall measured resistance will remain within the expected range. Measurements indicate that resistance exceeds the expected range until the conductor has lost most of its structural integrity. Thus resistance remains within the expected range even when only a fraction of the conductor is intact. For this reason, resistance measurements are insensitive to partial loss of conductor integrity. Further, resistance measurements have limited specificity. A single, out-of-range value may be an artifact, and marked increases can occur at the electrode-myocardial interface.

Hafelinger et al (U.S. Pat. No. 5,003,975) and Cinbis et al (U.S. Pat. No. 5,897,577) summarize some of these methods, which include measurements made directly using either a single pacing pulse or a single independent pulse used only for measuring resistance. McVenes et al (U.S. Pat. No. 5,741,311) describe use of a longer burst of alternating current at a single frequency. The purpose of these longer (about 100 ms) pulses is to drive the system to a steady-state condition that is not achieved by single, short (less than 1 ms) pacing pulses. Schuelke et al (U.S. Pat. No. 5,755,742) describe a method for measuring resistance of defibrillation electrodes by applying a test voltage applied to a different excitation current pathway. Kroll et al (U.S. Pat. No. 5,944,746) described an automated method for periodic measurement of the resistance of the high-voltage (defibrillating) coil in ICD electrodes. Gunderson et al. (U.S. Pat. No. 7,047,083) described a method and system for automated, periodic, measurements of resistance in conductors attached to an ICD or pacemaker. However, these types of "impedance monitoring," which return values close to direct current resistance, identify lead anomalies before inappropriate shocks in only about a third of ICD patients who have conductor fractures.

A newer method for monitoring ICD lead integrity is based on the response of ICD pulse generators to electrical "noise" signals associated with lead conductor fractures. These nonphysiological signals have specific characteristics that differentiate them from true cardiac signals such as high variability and, at times, nonphysiologically-rapid rates. If these signals are of sufficient amplitude and exceed the ICD's dynamically-changing sensing threshold, the ICD oversenses them. Repetitive oversensing of nonphysiologically-short intervals may indicate lead conductor fracture even if lead resistance is normal. Gunderson et al. (U.S. Pat. No. 7,289,851) described a Lead-Integrity Alert that incorporates both ICD-based measures of oversensing based on the nonphysiologically-rapid rate of sensed signals and periodic measurements of resistance. This method, combined with automatic ICD reprogramming, improves warning time before inappropriate shocks caused by lead-related oversensing. Nevertheless, approximately 25% of patients receive less than 3 days of warning, and some receive almost no warning.

This method detects only some lead-noise signals. It cannot detect a lead anomaly unless it generates signals that are both fast enough and of sufficient amplitude to be classified as nonphysiological oversensing. Thus it will not detect a lead anomaly if it does not generate "noise signals" or it generates only low-amplitude noise signals, or signals that do not occur at a fast enough rate.

Gunderson et al. (U.S. Pat. No. 7,369,893) further describe a method for withholding delivery of ICD shocks if ventricular fibrillation is detected from analysis of the pace-sense lead, but not confirmed by analysis of the high-voltage lead. Although not yet evaluated in patients, this method is expected to further reduce unnecessary shocks. However, it requires sufficient oversensing to result in inappropriate detection of ventricular fibrillation clinically. Thus it does not provide early diagnosis of conductor anomalies. Withholding shocks for ventricular fibrillation detected on the near-field electrogram has an inherent risk of withholding life-saving therapy, however small, and is thus not the preferred approach to diagnosis of conductor fracture. Like the Lead-Integrity Alert, it is not applicable to intraoperative diagnosis or to pacemakers and neurostimulators.

Additionally, no presently-used method reliably warns before loss of pacing function for bradycardia pacing support, antitachycardia pacing, or cardiac resynchronization pacing.

In addition to limited sensitivity, present methods for diagnosing lead conductor anomalies have limited specificity resulting in false positive diagnostics. Evaluation of false positive diagnostics adds cost and work to medical care and may contribute to patient anxiety. If a false-positive diagnostic is not diagnosed correctly, patients may be subject to unnecessary surgical lead replacement with its corresponding risks. In the only report on this subject, 23% of leads extracted for the clinical diagnosis of lead fracture tested normally after explant.

Any clinical method for detecting conductor anomalies in implanted leads must make measurements while the conductor and lead are in the body. Typically, the measuring circuit includes the conductor-tissue interface in the body. Thus the measured values will depend both on the behavior of the conductor being evaluated and the conductor-tissue interface. Warburg (1899) was one of the first to study frequency-dependent properties of the electrode-electrolyte interface. Geddes (1972) reviewed this subject extensively and (1971) studied the frequency response of stainless steel electrodes used for research. De Boer and van Oosterom (1976) studied the frequency response of platinum electrodes used in research. In their appendix, they derive the time course of voltage and current response to a transient input signal as a function of the frequency-dependent properties of the equivalent circuit. These works are incorporated by reference herein.

Circuits for measuring impedance at varying test frequencies are known in the prior art. See for example *Agilent Impedance Measurement Handbook A guide to measurement technology and techniques 4th Edition* or Johnson (U.S. Pat. No. 3,599,055), which are incorporated by reference herein in their entirety.

Methods for evaluating the integrity of conductors and insulators have been developed for other fields, especially the electrical power and semiconductor industries. For example, the time delay of a signal reflected from faults in power transmission lines is used to determine the distance to the fault (for example U.S. Pat. No. 4,766,549 to Schweitzer, III, et al.). Stewart et al (U.S. Patent Application 2008/0309351) describe a sensor for monitoring of high-voltage insulation (used in power generation, transmission, or distribution systems) that includes the time course ("shape") of a response to a transient input. Bechhoefer and Sadok (U.S. Pat. No. 7,120, 563) describe a method for wire-fault detection, citing as applications the aircraft and aviation industries. In their method, signals from a wire are analyzed to determine if they are characteristic of an intact wire or a faulty wire. Kwon et al (2009) describe a method for early detection of degradation of solder joints using differences in response to direct current and radiofrequency signals.

For these and other reasons, a need exists for the present invention.

SUMMARY OF THE INVENTION

The present invention provides a method and apparatus for diagnosis of conductor anomalies that can be used to diagnose conductor anomalies in leads attached to an implantable medical device, such as a pacemaker, ICD, or neurostimulator. The method and apparatus of the invention are practical, reliable, accurate and efficient, and are believed to fulfill and need and to constitute an improvement over the background technology.

The method discriminates leads with conductor anomalies from normally-functioning leads based on measures of dynamical, anomaly-induced changes in conductor capacitance and inductance. The method may be implemented in the pulse generator, a device programmer, a pacing-system analyzer, or a testing apparatus for explanted leads.

A fundamental principle of the Lead Anomaly Detector is that an early-stage conductor anomaly will alter conductor inductance or capacitance, causing a detectable change in a measured parameter that depends on a dynamical property such as susceptance, the ability of a conductor or capacitor to pass alternating current. The measured parameter is thus sensitive to the presence of a conductor anomaly. Increases in conductor inductance result in frequency-dependent changes in susceptance that increase impedance as a function of increasing frequency. Increases in conductor capacitance result in susceptance changes that decrease impedance as a function of increasing frequency.

In one aspect, the invention provides a method comprising the steps of:
a. delivering one or more signals to one or more conductors in a lead attached to a pulse generator,
b. measuring one or more parameters determined by the inductance or capacitance of the one or more conductors,
c. determining at least one relationship between two or more measured parameters,
d. comparing the at least one relationship to a predetermined expected range of relationships, and
e. detecting an anomaly based on a change between the determined and expected relationships.

In another aspect, the invention provides an apparatus, comprising:
a. a lead with one or more conductors, and
b. a pulse generator including a Lead Anomaly Detector including a Lead Anomaly Measurement SubSystem and a Lead Anomaly Analysis SubSystem.

The aspects, features, advantages, benefits and objects of the invention will become clear to those skilled in the art by reference to the following description, claims and drawings.

BRIEF DESCRIPTION OF THE DRAWINGS

The present invention, and the manner and process of making and using it, will be better understood by those skilled in the art by reference to the following drawings.

DETAILED DESCRIPTION OF THE INVENTION

Figure 1:
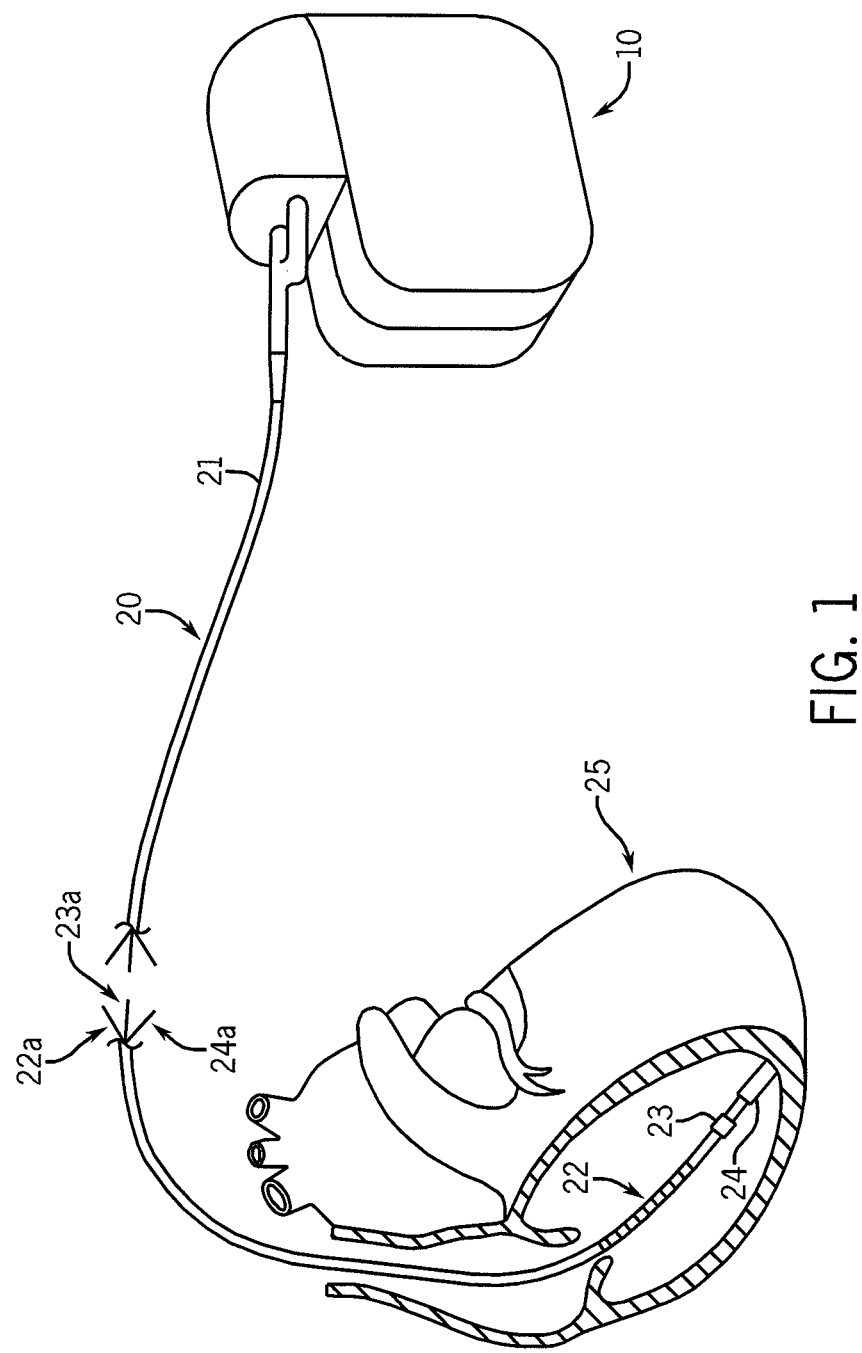
FIG. 1 shows an exemplary implantable medical device in which an embodiment of the present invention may be practiced. It shows an ICD pulse generator connected to a patient's heart via a transvenous lead used for pacing and defibrillation.

The method and apparatus of the present invention provides early and accurate diagnosis of conductor anomalies. One application applies to diagnosis of conductor anomalies in leads 20 attached to an implantable medical device with a pulse generator, such as an ICD 10. Referring to FIG. 1, the pulse generator 10 includes the system of the present invention that can perform automated, periodic measurements for any or all of the conductor pathways in the lead system 20. The lead system 20 comprises an elongated body 21 enclosing conductive leads 22a, 23a, and 24a extending to coil 22, ring 23 and tip 24, respectively. In this exemplary application, the ICD 10 is implanted in the chest of a human patient, and the lead 21 extends to the heart 25. The lead 21 may be implanted intra-cardiac as shown, but may alternatively be deployed intravascularly or subcutaneously.

Other applications of the system of the invention include, but are not limited to, an implantable pacemaker, an implantable neurostimulator, and a programmer or pacing-system analyzer used for testing of leads.

Figure 2:
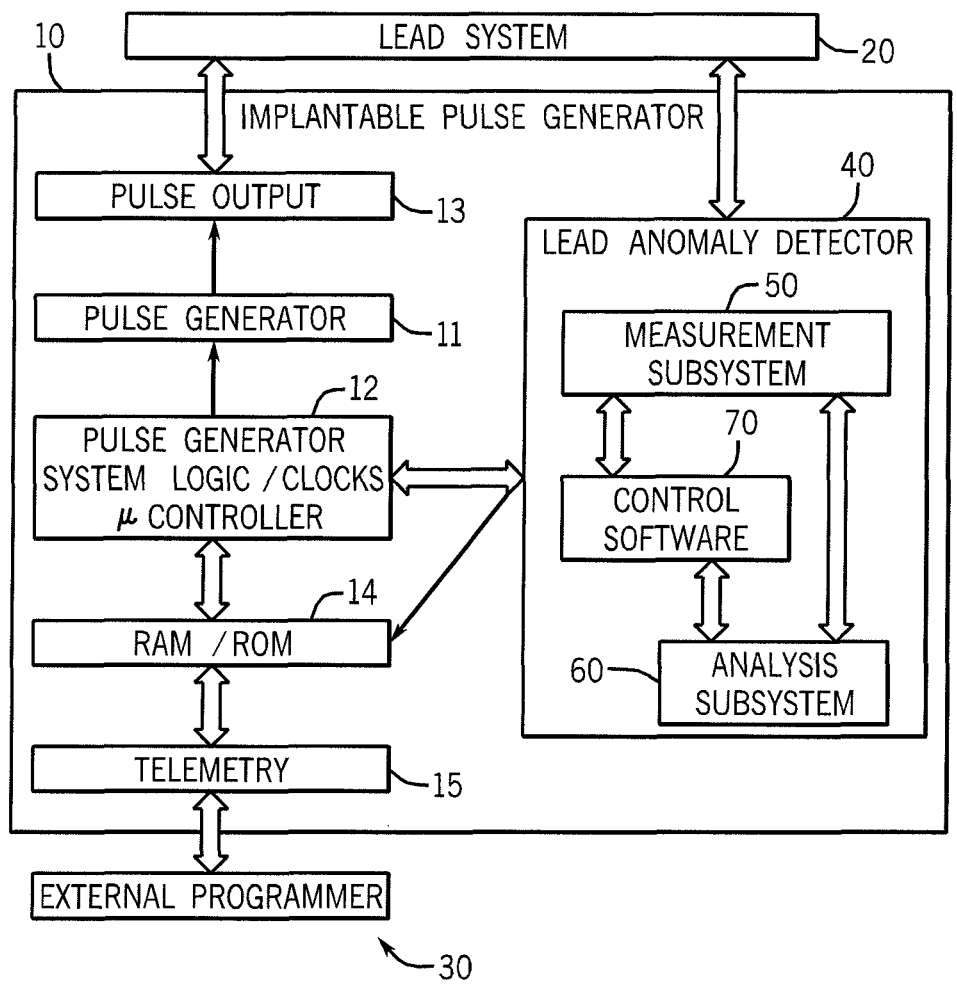
FIG. 2 is a top-level operational diagram of an embodiment of the system of the invention, including an embodiment of a Lead Anomaly Detector of the invention.

FIG. 2 illustrates the top-level operational flow-chart of the Lead Anomaly Detector system 40 deployed in the ICD 10. The ICD 10 includes a pulse generator 11, a controller 12, a pulse output assembly 13, RAM/ROM 14, and a telemetry assembly 15. The telemetry system 15 enables communication with an external programmer 30 A preferred embodiment of the Lead Anomaly Detector 40 comprises three primary system elements: (1) a Lead Anomaly Measurement SubSystem 50, (2) a Lead Anomaly Analysis SubSystem (LAAS) 60, and (3) Lead Anomaly Control Software (LACS) 70. The Lead Anomaly Measurement SubSystem 50 performs periodic measurements as described below to identify conductor anomalies.

Figure 4:
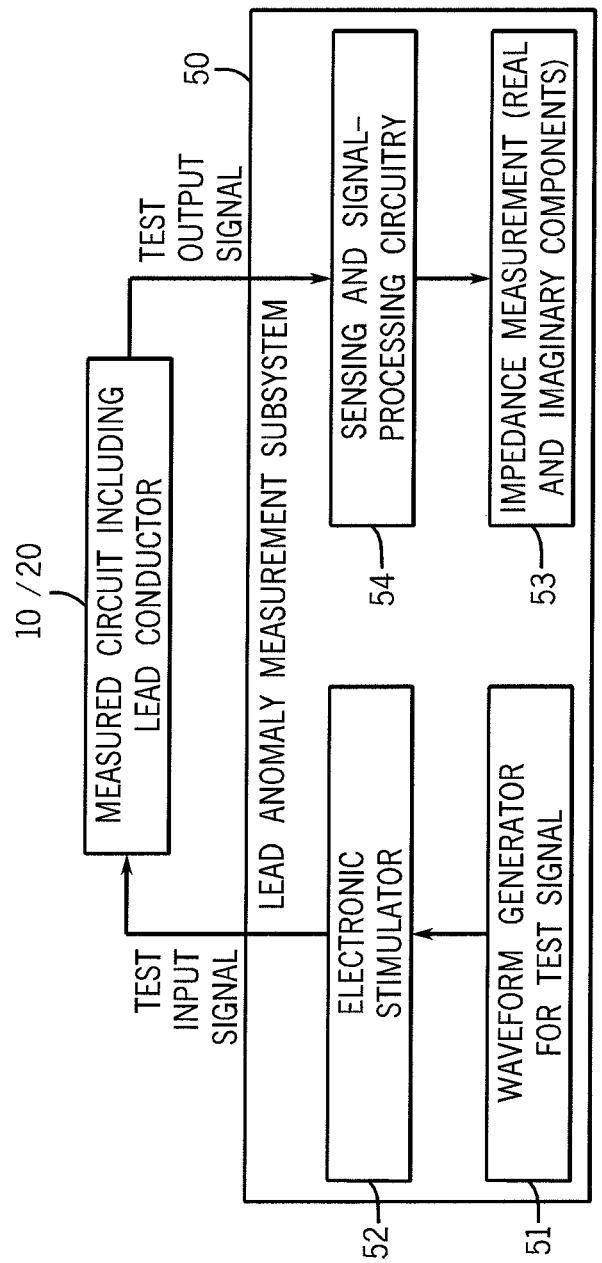
FIG. 4 is a top-level block diagram of an embodiment of the Lead Anomaly Measurement SubSystem.

FIG. 4 shows a preferred embodiment of the Lead Anomaly Measurement SubSystem 50 including a signal generator 51 capable of generating an appropriate signal or appropriate base and test signals and a mechanism 52 for delivering the input test signals to one or more of the conductors in the lead 21. It also includes a measurement subsystem 53 that measures suitable electrical parameters of the conductor during a sequence of one or more test signals. It preferably further contains a sensing and signal-processing subsystem 54 to filter or otherwise condition the output signal before it is measured.

Figure 3:
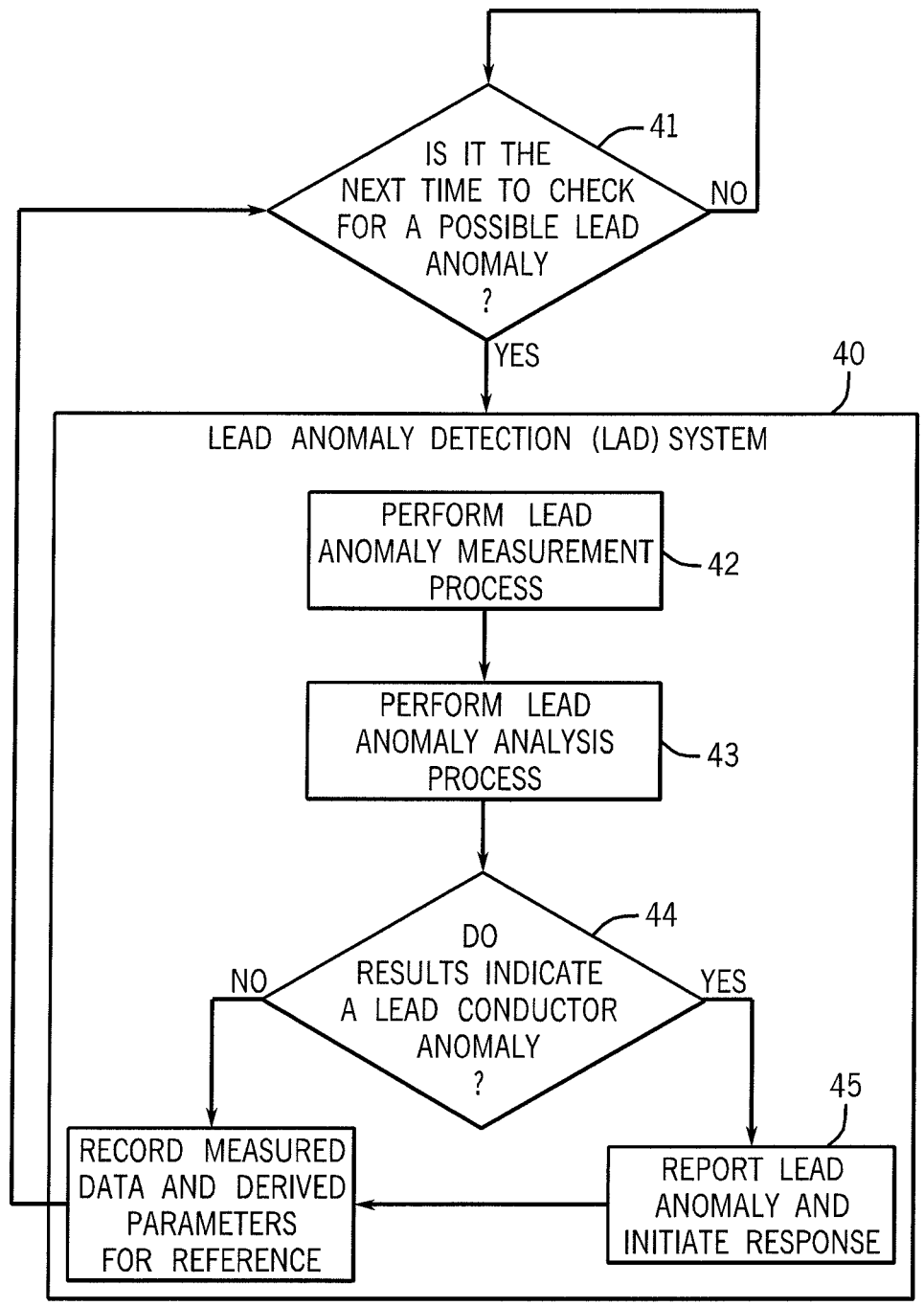
FIG. 3 is a top-level diagram of an embodiment of the Lead Anomaly Detector including a Lead Anomaly Measurement SubSystem, Lead Anomaly Analysis SubSystem, and Lead Anomaly Control Software within an implantable pulse generator.

FIG. 3 shows an embodiment of the method of use of the lead anomaly detection system 40 comprising the step of first determining whether it is time to check for a possible lead anomaly 41. If it is, then the steps of performing a lead anomaly measurement 42, performing a lead anomaly analysis 43, and determining whether the results of the analysis 43 indicate a lead anomaly 44 are taken. If a positive indication exists, then a lead anomaly is reported and a response is initiated 45. If a negative indication exists, measured data and derived parameters are recorded for reference 46. The process then returns to step 41 awaiting the time for the next check.

Figure 5:
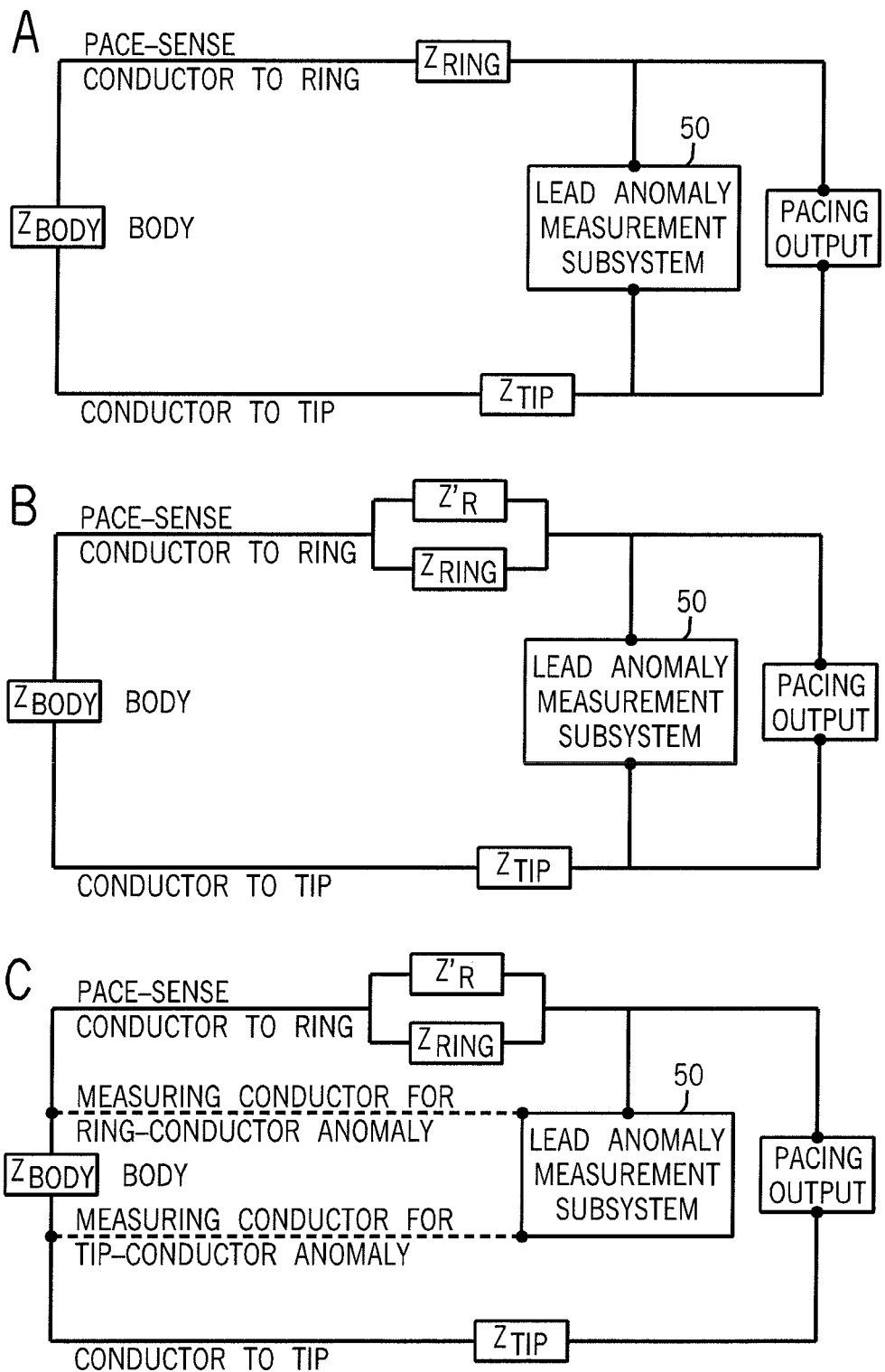
FIG. 5 is a high-level diagram showing an embodiment of a circuit to which the Lead Anomaly Measurement Subsystem may be applied, showing an anomaly in the conductor to the ring electrode of a pacemaker lead.

The measured signal may be the transmitted signal, the signal reflected from the anomaly, or both. The circuit measured may include a single conductor being tested alone, two conductors, or two conductors and the patient components of the circuit including blood and/or tissue. In the diagram of FIG. 5, the upper panel (A) shows a block diagram of the pace-sense components of a pacemaker or ICD lead 21 in the body. The upper panel (A) shows an intact lead 21. $Z_{Ring}$ and $Z_{Tip}$ represent impedances of the conductors 23a and 24a to the ring and tip electrodes 23 and 24, respectively; and $Z_{Body}$ represents the impedance of the body tissue in the circuit. These impedances are primarily resistive loads, with capacitive and inductive elements. Typical resistance values are about 15-30Ω for $Z_{Ring}$ and $Z_{Tip}$ and about 300-1000Ω for $Z_{Body}$, depending on the specific lead used. The middle (B) and lower (C) panels introduce $Z'_{Ring}$, which represents abnormal impedance introduced by an anomaly of the conductor 23a to the ring electrode 23. $Z'_{Ring}$ has substantial capacitive and inductive elements. In the middle panel (B), the Lead Anomaly Measurement SubSystem 50 measures values related to the entire circuit. This is the typical configuration for measurement circuits applied to existing pacemaker and ICD leads. The lower panel (C) shows an optional embodiment that includes a novel lead design in which one or more additional conductors, represented by the dashed line segments, connects the near the distal end of the pace-sense conductors in the patient. These additional conductors permit the Lead Anomaly Measurement SubSystem 50 to isolate each pace-sense (or defibrillation) conductor and thus perform measurements on a circuit that includes only the conductor being measured and the measurement conductor, removing contributions to impedance from the body and the electrode-tissue interface.

The Lead Anomaly Measurement SubSystem 50 will deliver signals when the patient is in normal or bradycardia-paced rhythm, either immediately after pacing pulses that capture the cardiac chamber of interest or sensed, spontaneous activation of said chamber. Thus base and test signals will be delivered in the absolute refractory period. In one embodiment, they will be sufficiently short that they end in the absolute refractory period of ventricle in all patients and of the atrium in almost all patients, generally not longer than 100 ms. They will also be of sufficiently low amplitude that the risk of capturing the heart is minimal, even if they are delivered at an incorrect time. If multiple test signals are delivered, they will be separated from the base signal and from each other by a minimum time interval and/or number of cardiac cycles, generally in the range of 2-20 seconds or 2-20 cardiac cycles.

The Lead Anomaly Analysis SubSystem (LAAS) 60 compares one or more recently measured electrical parameters with one or more previously measured electrical parameters to determine if a lead anomaly is present. It includes a computer or microprocessor that compares the values of measured electrical parameters with a range of nominal values for the lead. The computer may store a library of conductive properties known to be characteristic of normally-functioning conductors and one or more specific types of conductor anomalies, such as partial fracture, complete fracture, or insulation failure. It may also store the history of these values for the specific conductor implanted in the specific patient and use this history to construct a range of expected values for the patient and conductor as described by Gunderson et al (U.S. Pat. No. 7,047,083) for lead resistance. The expected range of the measured parameter will be established empirically for normal function of a given conductor, combination of conductors in lead, or one or more conductors in a specific patient. If one or a sufficient number of measured values fall outside this expected range, the Lead Anomaly Analysis SubSystem 60 detects a lead-conductor anomaly. One of the hallmarks of "noise" signals generated by lead conductor anomalies is their variability. Thus, the testing process is repeated at predetermined intervals, and the presence of a conductor anomaly is detected if the variability of one or more measured parameters exceeds a predetermined threshold value.

If a conductor anomaly is identified, the Lead Anomaly Analysis SubSystem 60 generates a response, which may include—but is not limited to—one or more of the of the following: notifying the patient via an alert mechanism, notifying the health-care provider via the same or different alert mechanism, and altering values of the pulse generator's programmable parameters in response to the specific anomaly detected. The purpose of these responses is to increase the likelihood of pulse generator function and/or minimize the likelihood of adverse device consequences such as loss of pacing function or inappropriate shock from the ICD 10.

Figure 6:
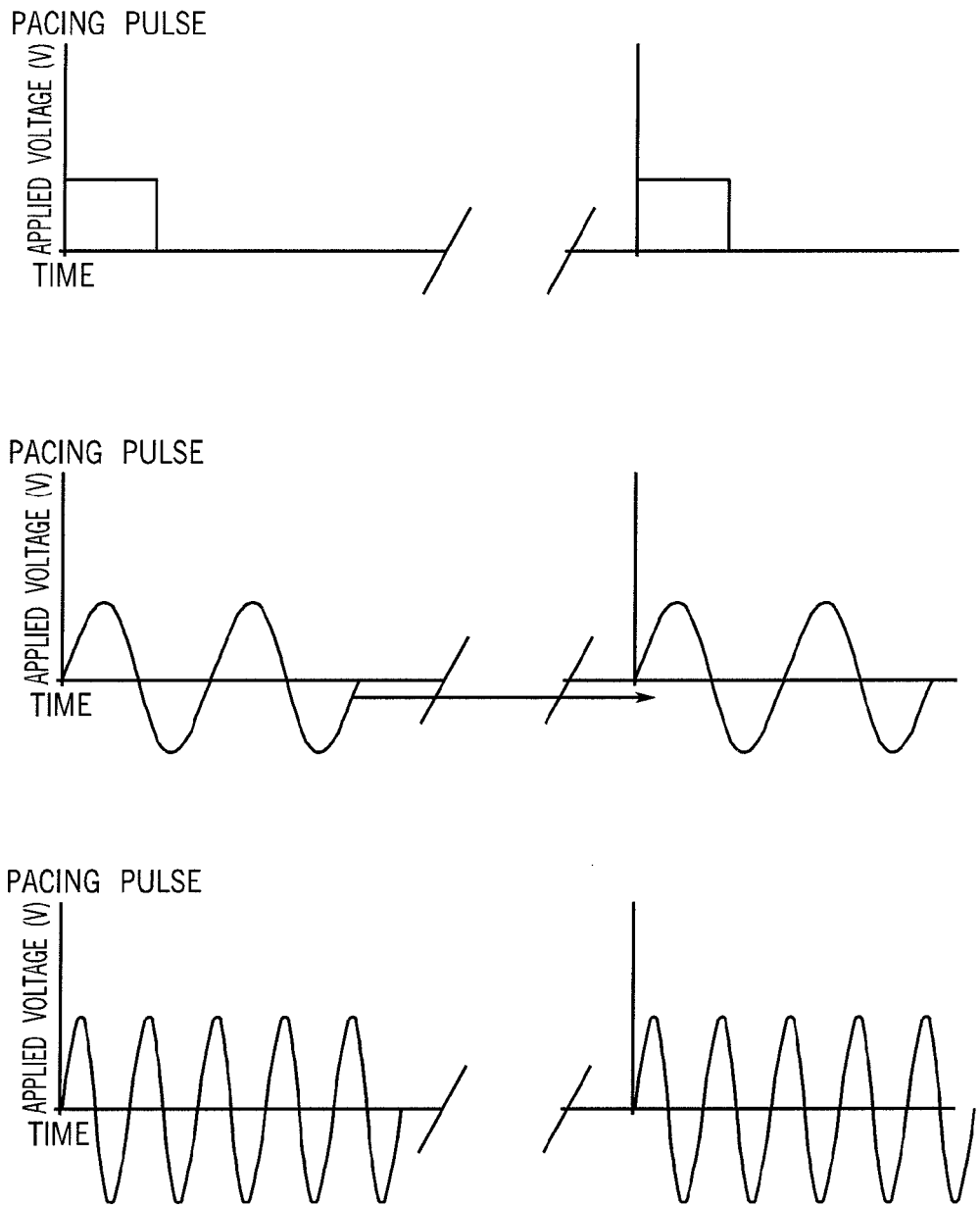
FIG. 6 is a timing diagram that depicts delivery of a narrow pacing pulse followed by Lead Anomaly Detector pulses delivered at a base frequency and one or more test frequencies.

One embodiment measures frequency-dependent parameters such as the real and imaginary components of impedance (or signal amplitude and signal phase-angle) during a base signal and one or more test signals delivered at frequencies different from the base signal. FIG. 6. illustrates delivery of a short square wave test signal (upper panel) and sinusoidal test signals at 2 different frequencies (middle and lower panels). To ensure consistent data, each test signal may be repeated one or more times, and the results may be accepted as valid only if the results for each signal are sufficiently reproducible.

Test signals delivered at multiple frequencies can be used to construct an "impedance map" or "phase-angle map" as a function of applied frequency. For example, if the test signal is delivered using alternating current frequency with (f) in a circuit with resistance (R), capacitance (C), and inductance (L), the impedance (Z) is given by:

$$Z = \sqrt{(R^2 + (X_L + X_C)^2}$$

where
$X_L = \omega L$
and the applied angular frequency ($\omega$) is defined as $\omega = 2\pi f$.
Further, the voltage in the circuit is phase shifted by the phase angle $\phi$ given by $$\phi = \tan^{-1}\left(\frac{X_L - X_C}{R}\right).$$

Thus both the measured impedance and phase of the test signal will vary as a function of the test signal's frequency. Further, the circuit's natural angular resonance frequency will be given by:

$$\omega = \sqrt{\left(\frac{1}{LC} - \frac{R^2}{4L^2}\right)}$$

Figure 7:
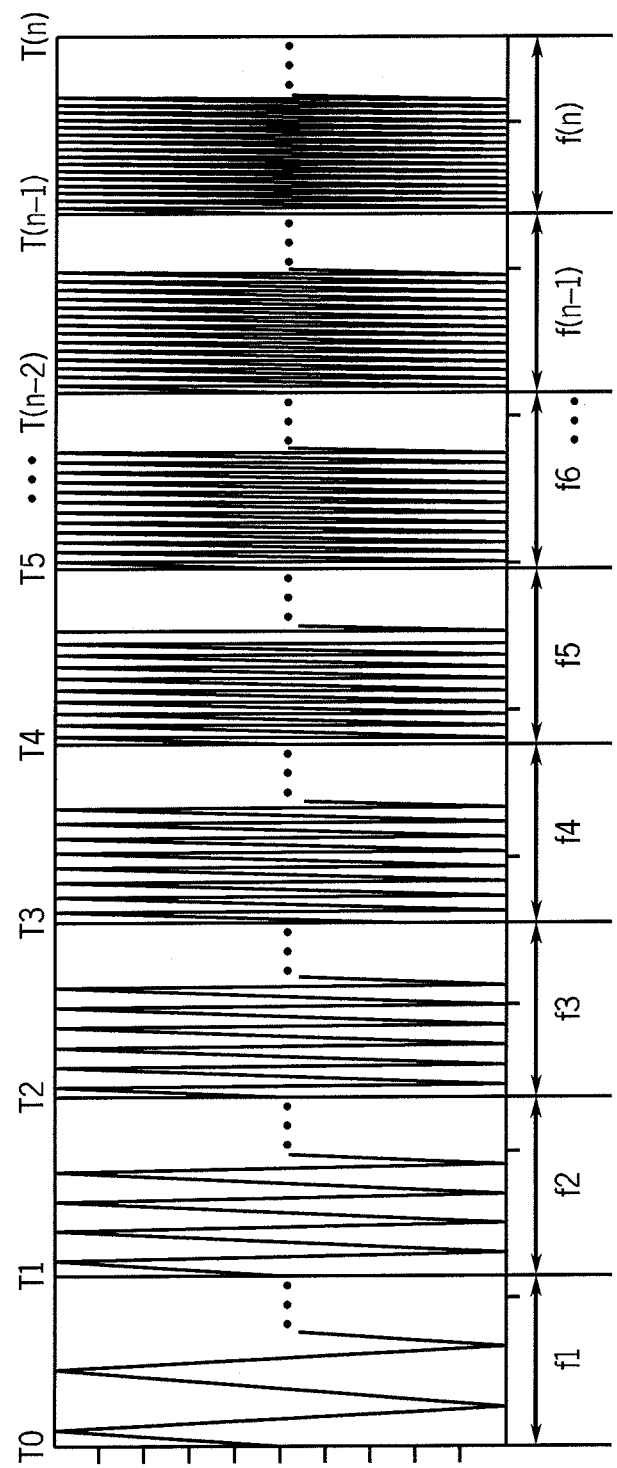
FIG. 7 illustrates a frequency sweep of test pulses delivered at increasing frequencies.

In this embodiment of the Lead Anomaly Measurement SubSystem 50, base and test signals are delivered at a subset of frequencies to perform a frequency sweep. At a pre-determined time, the Lead Anomaly Control Software 70 initiates a next anomaly detection cycle. First, it defines and then constructs required instructions for the Lead Anomaly Measurement SubSystem 50. These instructions include sweep parameters for this next anomaly detection cycle. Examples of these parameters include time parameters and frequency parameters. Time parameters may include the start time for the sweep (T0), the time duration for each sweep frequency ($\Delta$T), and the start time for the final frequency (T(n−1)). Referring also to FIG. 7, frequency parameters may include the value for the first frequency in the sweep (f1), the frequency difference between successive frequencies during the sweep ($\Delta$f), and the value for the final frequency (f(n)).

Then the Lead Anomaly Control Software 70 actives the Lead Anomaly Measurement SubSystem 50 and provides it with the necessary sweep parameters. Following these instructions, the Lead Anomaly Measurement SubSystem applies a frequency sweep across a circuit that includes the conductor being measured and collects data for each frequency in the sweep, such as the real and imaginary components of impedance.

The Lead Anomaly Analysis SubSystem 60 then processes the measured data and compares it against data from either a plurality of previous impedance sweeps or a library of stored ranges for normally functioning conductors and/or conductor anomalies. It may perform these comparisons either using directly measured data or using derived variables, such as a vector combining data recorded for multiple frequencies in the sweep.

As an illustrative example, the electronics for the impedance measurement steps of the Lead Anomaly Measurement SubSystem 50 are implemented using a chip such as the Analog Devices AD5933 fully integrated single-chip impedance measurement device (Analog Devices AD5933 Data Sheet 2004, incorporated herein by reference in its entirety). The AD5933 is a high-precision impedance-converter system that combines an on-board frequency generator with a 12-bit, analog-to-digital converter (ADC). The frequency generator provides an excitation voltage to an external complex impedance at a known frequency. The response signal (current) is sampled by the on-board, analog-to-digital converter, and a discrete Fourier transform is processed by an on-board digital signal processing (DSP) engine. The discrete Fourier transform algorithm returns real and imaginary words at each output frequency, effectively implementing spectroscopic impedance measurements. The magnitude and relative phase of the impedance at each frequency point along a sweep are calculated.

The AD5933 applies a sinusoidal signal as excitation to an external load consisting of a circuit that includes the conductor being measured. The sinusoidal signal is constructed on-board using standard direct digital synthesis (DDS) techniques. The clock for the direct digital synthesis can be generated using one of several methods such as a reference clock external to the AD5933 (internal to the pulse generator or programmer), an on-board RC oscillator, or an on-board phase lock loop technique, As described previously, the Lead Anomaly Control Software 70 programs the conditions required for the sweep—including the start frequency, frequency step size, and the stop frequency—and then issues a "start" command to the AD5933 (or to alternative impedance-measuring components) to initiate the sweep and impedance measurement process. At each frequency on the sweep, the on-board analog-to-digital converter acquires 1024 samples and calculates a discrete Fourier transform to provide the real and imaginary components of the circuit's impedance at the measured frequency. These data are available at each sweep point (test frequency) to the Lead Anomaly Measurement SubSystem 50 controller through a serial port interface. The impedance is calculated at each frequency point in the sweep and two plots are created. The first plot is a frequency versus magnitude plot, and the second plot is a frequency versus phase plot. A derived plot of phase angle vs. magnitude may also be constructed. Measured signals or quantities derived from them, such as elements of the phase angle vs. magnitude plot, are compared with reference values to detect lead anomalies.

A second embodiment of the testing process is based on the effect of capacitive and inductive circuit elements on the response to a transient input ("impulse") function. If the test signal is an impulse function, it is well known in the art that the voltage response of a series RLC circuit is given by:

$$v(t) = 2\sqrt{\frac{1}{LC}} \exp\left(-\frac{R}{2L}t\right)\cos\left\{\omega t + \tan^{-1}\left(\frac{2\omega L}{R}\right)\right\}$$

where $\omega$ is now the natural resonance angular frequency given by:

$$\omega = \sqrt{\frac{1}{LC} - \left(\frac{R}{2L}\right)^2}$$

As shown in the middle and lower panels of FIG. 5, the equivalent circuit has both series and parallel elements. However, these basic principles apply generally: A pure resistive circuit does not distort the input signal. Addition of a capacitive element prolongs the duration of the output signal before it reaches a predetermined fraction of the initial value. Addition of inductance results in an oscillatory response. As inductance increases, the frequency of the oscillations increases. Hence there is a decrease in the interval between baseline crossings and increase in the number of times the response signal crosses the baseline before reaching a predetermined fraction of its initial value. Thus the voltage or current response to an impulse function is sensitive to the inductance and capacitance introduced by the presence of conductor anomalies that do not change the conductor's resistance.

In this embodiment, the testing process applies a transient input signal to the circuit including the conductor, and one or more parameters related to the time course of the voltage or current response is measured. This time course is determined by the conductor's capacitance and inductance. In this embodiment, the Lead Anomaly Measurement SubSystem comprises (1) a signal generator capable of generating one or more types of transient, impulse test signals to one or more of the conductors in the lead and (2) a SubSystem that can measure the voltage and/or current response to the test impulse at multiple time intervals to determine the voltage/ and or current response as a function of time.

A third embodiment of the testing process is based on the effect of capacitive and inductive circuit elements on the response to an input signal of finite, known duration. For example, if a rectangular pulse with a fixed voltage is applied to a circuit containing only a resistor, the current in the circuit reaches its maximum value immediately. But if the circuit contains inductance and capacitance, the measured current increases gradually over time, reaching a maximum value at the end of the pulse. The time course of the current increase may be used to identify the magnitude of capacitive and inductive circuit elements. The actual measured current may be sampled frequently or continuously, or at only a few points, such as a predetermined fraction of the pulse duration and the end of the pulse.

The present method has specific advantages over methods now in use. The currently-used resistance measurement remains within the normal range if only part of the conductor is intact and is thus insensitive to partial loss of conductor integrity. In contrast, the present method detects inductance and capacitance changes directly related to the presence of a conductor anomaly. Currently-used measures of oversensing depend on recording the intermittent noise signals generated by lead anomalies. They identify a subset of these noise signals that have high enough amplitude to be sensed and fast-enough rate that they do not likely represent physiological events. In contrast, the present method does not require the lead anomaly to generate any signals.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A method for determination of anomalies in a lead implanted within a patient, the method comprising the steps of:
   a. delivering one or more signals at a subset of frequencies to one or more conductors in the implanted lead,
   b. measuring two or more frequency dependent parameters determined by inductance or capacitance of the implanted lead,
   c. determining at least one relationship between two or more measured parameters,
   d. comparing the at least one relationship to a predetermined expected range of relationships, and
   e. detecting an anomaly in the implanted lead based on a change between the determined and expected relationships, wherein the anomaly can be any of a partial conductor fracture, a complete conductor fracture, a partial insulation failure, and a complete insulation failure.

2. The method of claim 1 in which the lead is attached to a pulse generator in an implantable cardioverter defibrillator (ICD) or a pacemaker, and wherein the lead is implanted intracardiac, intravascularly, or subcutaneously.

3. The method of claim 2, further comprising the step of responding to the detection of the anomaly.

4. The method of claim 1 in which the measured parameter is measured from a reflected signal.

5. The method of claim 1 in which the at least one relationship is a mathematical relationship.

6. The method of claim 5 in which the mathematical relationship is a ratio or difference.

7. The method of claim 1 in which:
   a. one or more derived numerical results are calculated for each comparison, and b. the presence of an anomaly is detected by comparison of the values of the derived numerical results to a range of expected values.

8. The method of claim 1, that:
a. delivers a base signal and one or more test signals at different frequencies to one or more conductors in a lead attached to a pulse generator,
b. measures values of frequency-dependent parameters of the conductors during a base signal and one or more test signals with different test-signal frequencies,
c. determines a relationship or relationships between or among two or more of the measured values,
d. compares the relationships to an expected range of relationships,
e. detects an anomaly based on a change between the determined and expected relationships, and
f. responds to the detection of the anomaly.

9. The method of claim 8 in which:
a. the parameter is determined using a base signal and a test signal at a different frequency, and
b. the relationship is the ratio of the value at these two frequencies.

10. The method of claim 8 in which the frequency-dependent parameters are a subset of the following parameters: complex impedance including real and imaginary components, admittance, susceptance, resonance frequency, and phase angle.

11. The method of claim 8 in which the frequency-dependent parameter is the resonance frequency.

12. The method of claim 8 in which the base signal is a single pulse.

13. The method of claim 12 in which the base signal is a pacing pulse itself.

14. The method of claim 8 in which the test signal is alternating current at frequency between 1 Hz and 1 GHZ.

15. The method of claim 1 in which a single test signal is delivered to a circuit including one or more conductors in a lead attached to a pulse generator.

16. The method of claim 3 in which the response is to change one or more of the pulse generator's programmed settings.

17. The method of claim 1 in which test signals are delivered at intervals on an automated, periodic basis.

18. The method of claim 17 in which the intervals are determined by the values of the measured parameters or the variability of these values.

19. The method of claim 1 in which
a. the variability of the measured values are determined, and
b. the presence of a conductor anomaly is detected if the variability exceeds a predetermined value.

* * * * *